United States Patent
Sakai et al.

(10) Patent No.: US 6,657,430 B2
(45) Date of Patent: Dec. 2, 2003

(54) NONCONTACT TYPE MAGNETIC HEAR WEAR-RATE MEASURING APPARATUS

(75) Inventors: Seiichi Sakai, Tokyo (JP); Hiroshi Yamauchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 10/041,999

(22) Filed: Oct. 25, 2001

(65) Prior Publication Data

US 2002/0105323 A1 Aug. 8, 2002

Related U.S. Application Data

(63) Continuation of application No. 09/124,641, filed on Jul. 29, 1998, now abandoned.

(30) Foreign Application Priority Data

Jul. 30, 1997 (JP) .............................................. 9-205100

(51) Int. Cl.$^7$ ......................... G11B 5/455; G01R 33/12; G01N 27/72
(52) U.S. Cl. ....................... 324/237; 324/210; 360/137
(58) Field of Search ...................... 324/207.15, 207.16, 324/210, 212, 229, 234, 236, 237, 238; 360/31

(56) References Cited

U.S. PATENT DOCUMENTS

| | | | | |
|---|---|---|---|---|
| 4,820,980 A | * | 4/1989 | Dodson-Edgars | .. 324/207.15 X |
| 5,729,133 A | * | 3/1998 | Sakai et al. | .................. 324/210 |
| 5,929,632 A | * | 7/1999 | Sakai | ......................... 324/210 |

* cited by examiner

*Primary Examiner*—Gerard R. Strecker
(74) *Attorney, Agent, or Firm*—Frommer Lawrence & Haug LLP; William S. Frommer; Dennis M. Smid

(57) ABSTRACT

A magnetic head wear-rate measuring apparatus for measuring the rate of head wear in noncontact form arranged to be opposed to a magnetic head and to serve as a part of oscillating elements of an oscillator circuit. A magnetic resistance of a magnetic circuit at a rotational position where the magnetic head faces the magnetic sensor, changes according to the degree of extension of the magnetic head from the surface of the drum, and the change in magnetic resistance acts as a variation in oscillating frequency. A counter is supplied with a pulse of a measured oscillating frequency and produces a pulse having a pulse width up to the counting of a predetermined number of pulses. The counter output is supplied to a second counter where the number of reference clocks lying within the pulse width is counted and used as measured data.

11 Claims, 15 Drawing Sheets

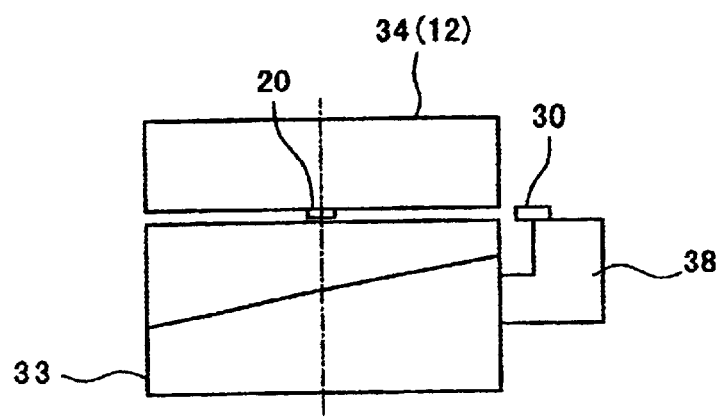
F I G. 2
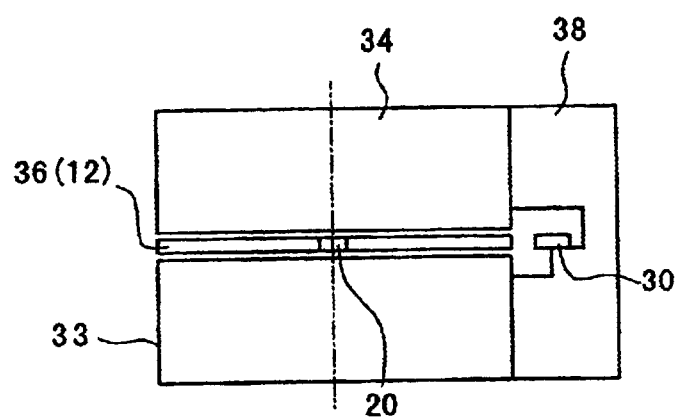
F I G. 3
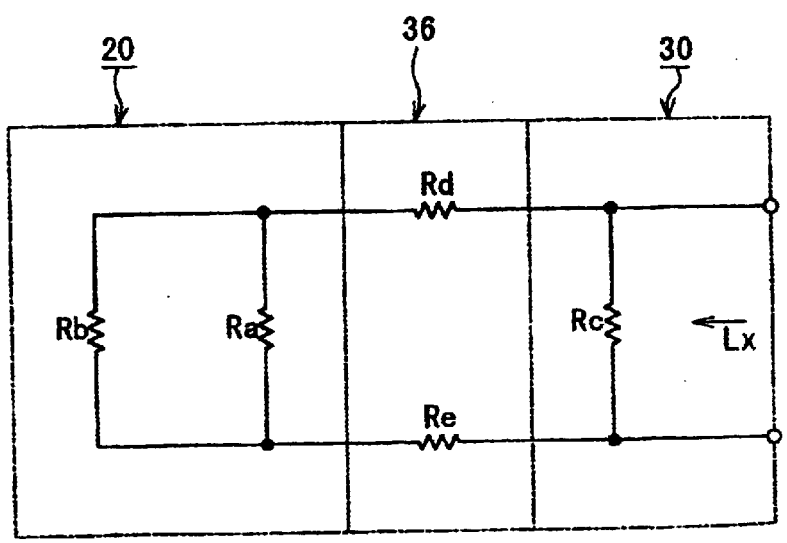
F I G. 5

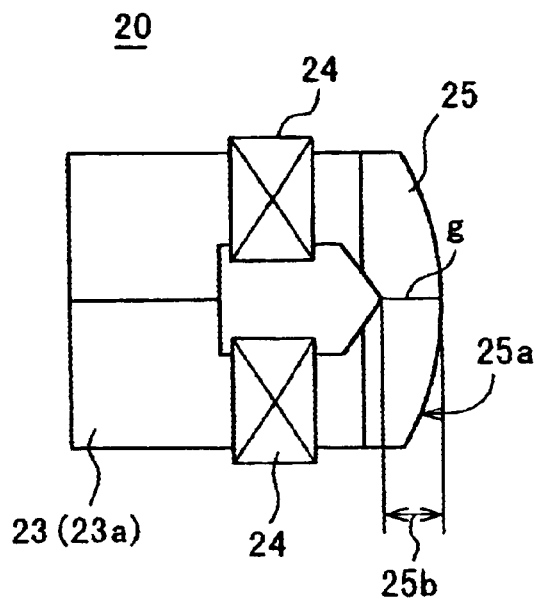
F I G. 4 (A)
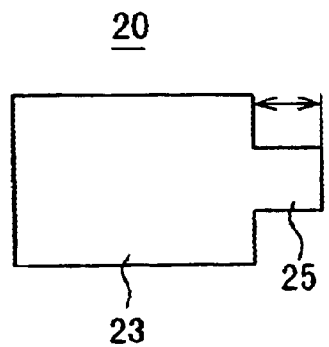
F I G. 4 (B)
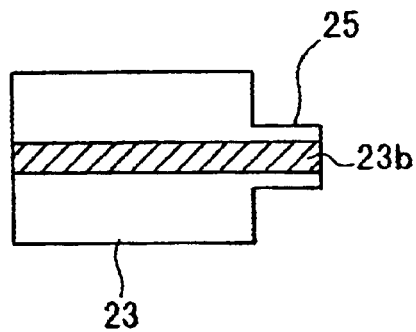
F I G. 4 (C)

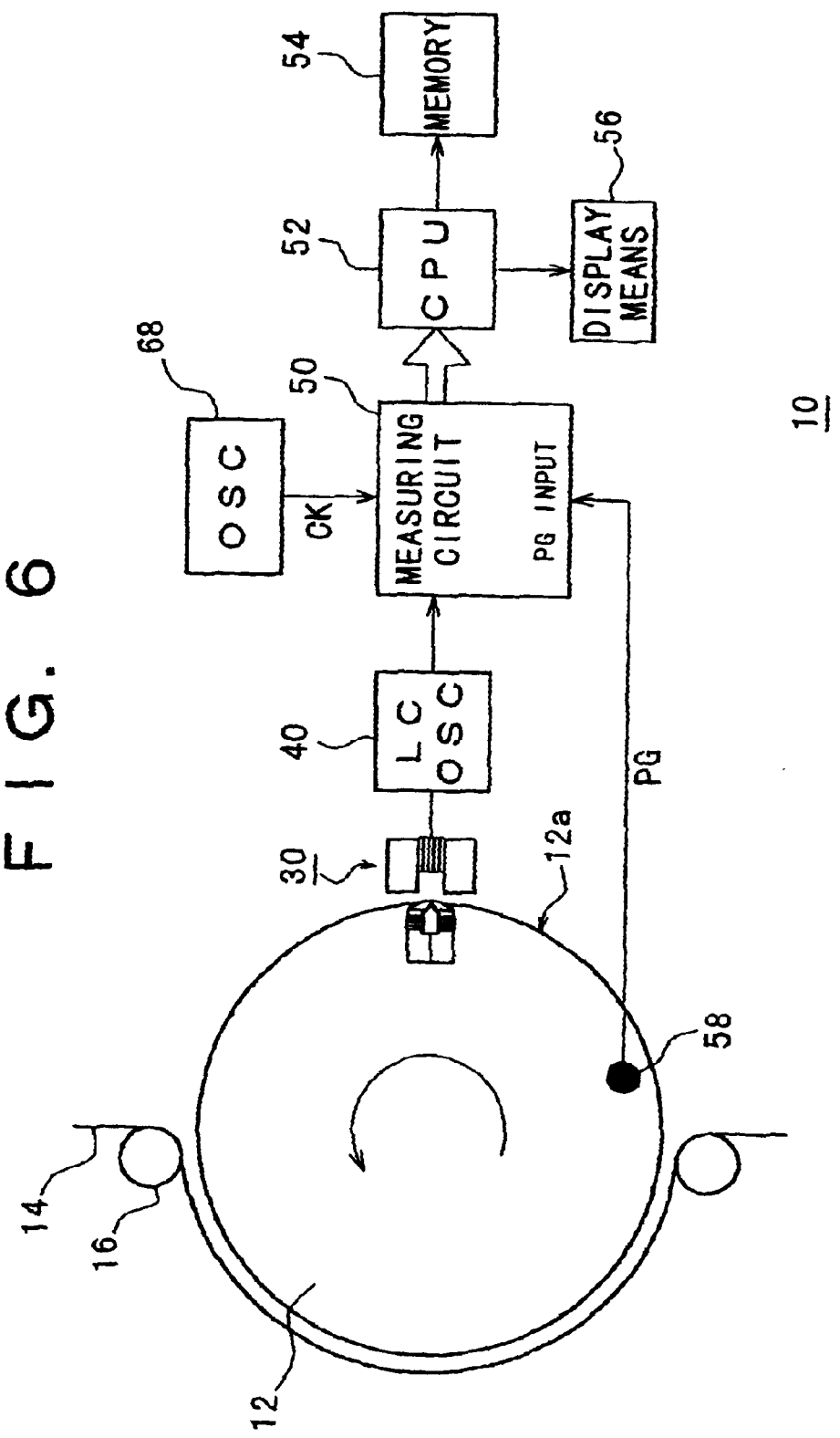

F I G. 7
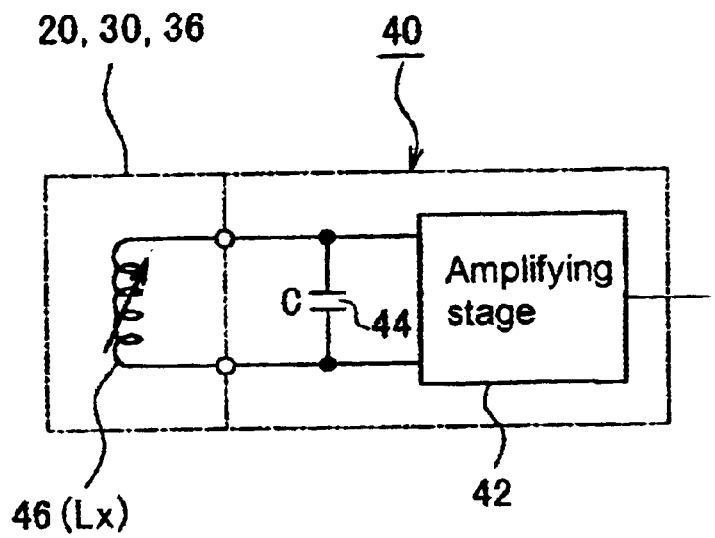
F I G. 9
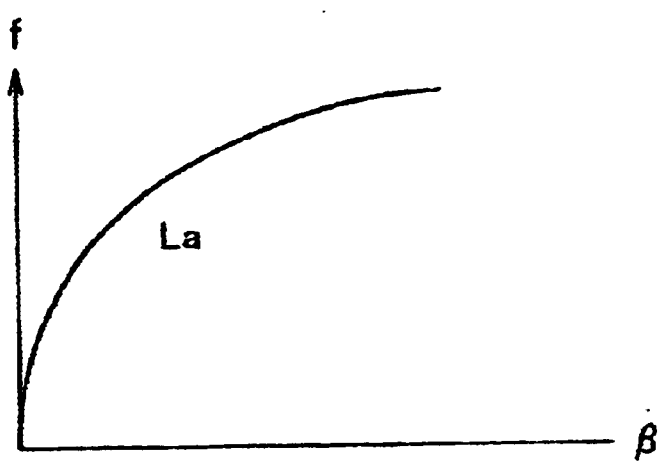

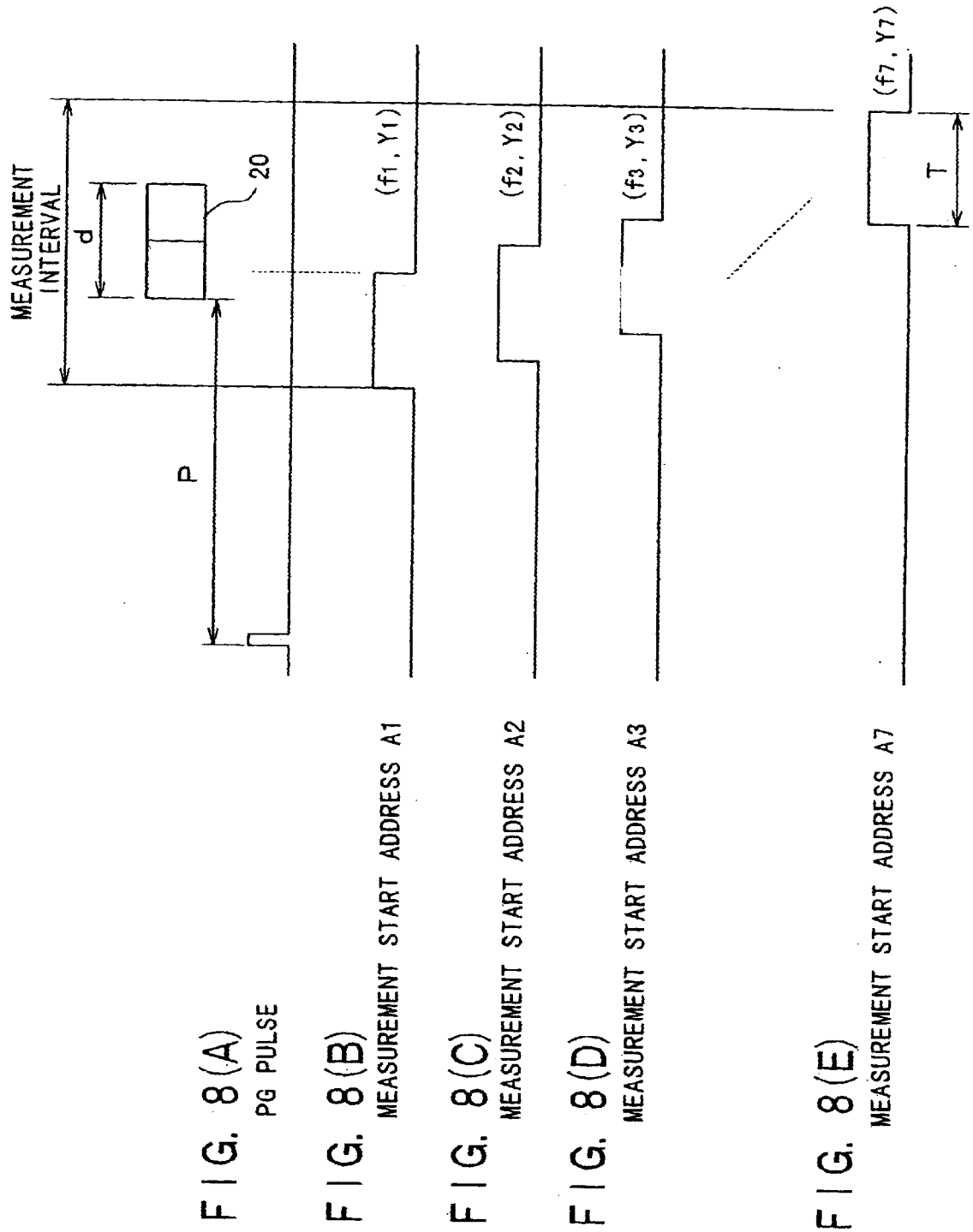

Hb=Ha+m4
Hc≒Hb

NONCONTACT TYPE MAGNETIC HEAR WEAR-RATE MEASURING APPARATUS

CROSS REFERENCE TO RELATED APPLICATIONS

This application is a Continuation of prior application U.S. Ser. No. 09/124,641, filed Jul. 29, 1998, now abandoned.

BACKGROUND OF THE INVENTION

1. Field of the Invention

This invention relates to a noncontact type magnetic head wear-rate measuring apparatus suitable for use in a rotating drum device using a magnetic head, such as a video tape recorder, a data recorder or the like.

More specifically, the present invention relates to a noncontact type magnetic head wear-rate measuring apparatus wherein a magnetic sensor is disposed in a state placed in noncontact with a rotating magnetic head device and the rate of wear of a magnetic head can be measured in a noncontact state and with high accuracy according to a variation in the total magnetic resistance between the magnetic head and the magnetic sensor.

2. Description of the Related Art

In AV devices each using a rotating drum device with a magnetic head mounted thereon, such as a video tape recorder (VTR), a data recorder, a digital audio tape recorder (DAT), etc., the magnetic head is relatively driven in a state of being in contact with the magnetic tape. Therefore, a tape sliding portion of the magnetic head wears out due to the running of the magnetic tape over a long period of time.

When the rate of wear thereof reaches several tens of microns, a region (head depth) for forming a magnetic head gap disappears in the case of a normal magnetic head. Therefore, there may be cases in which when the magnetic head wears till the instance preceding the complete disappearance of the head depth, such a magnetic head interferes with recording and reproduction. Further, when the head sliding portion wears out until the head depth completely disappears, the worst case occurs and hence a signal cannot be recorded and reproduced.

Since, in this case, a signal reproduced from the magnetic tape is brought to zero when the rate of wear of the head has reached several tens of microns during signal reproduction, a malfunction in the magnetic head can be immediately recognized.

However, when the rate of wear of the head has reached several tens of microns during recording of a signal, there is the risk that the signal cannot be normally recorded and important information may be excluded. This abnormal condition cannot be confirmed unless the recorded signal is reproduced. Thus, when the AV devices are used in particular as for commercial use, such a situation must be avoided.

Therefore, particularly when the rate of wear of the head employed in each AV device for commercial use is monitored and the rate of wear of the head reaches a predetermined value, the AV device preferably warns a user of its fact so as to urge the user to perform its maintenance and inspection. It is therefore necessary to measure the rate of wear of the head. In this case, however, a contact type measuring apparatus or a noncontact type measuring apparatus is considered as this type of measuring apparatus.

In the contact type magnetic head wear-rate measuring apparatus, a measuring jig such as a measuring element or probe is mounted to a magnetic head to be measured so as to come into contact with the magnetic head. Therefore, there is a possibility that a tape sliding surface of the magnetic head to be measured has flaws or the magnetic head or the magnetic head will break in the worst case. The result of measurements varies depending on how to mount the measuring probe to the magnetic head and an influence exerted on measuring accuracy cannot be overlooked.

When the rate of wear of a magnetic head to be measured is measured by the noncontact type magnetic head wear-rate measuring apparatus, the present measuring apparatus does not cause such a problem as produced in the contact type magnetic head wear-rate measuring apparatus. The noncontact type magnetic head wear-rate measuring apparatus measures the rate of wear of the head using light. In this case, a laser beam or the like is used as the light. Since the laser beam must be focused onto a tape sliding surface of the magnetic head so as to be accurately applied onto the tape sliding surface, the layout, adjustments and the like of a laser optical system become so troublesome. The measuring apparatus itself increases in volume due to the use of the optical system and a manufacturer gets greatly nervous at the assembly of the measuring apparatus into the rotating drum device.

SUMMARY OF THE INVENTION

An object of the present invention is to provide a noncontact type magnetic head wear-rate measuring apparatus capable of measuring the rate of wear of a magnetic head in a noncontact state and measuring the rate of head wear with high accuracy.

According to one aspect of the present invention, for achieving the above object, there is provided a noncontact type magnetic head wear-rate measuring apparatus, comprising:

magnetic sensor opposed to a rotating magnetic head device with a magnetic head mounted thereon and disposed in a state placed in noncontact with the rotating magnetic head device so as to fall outside an angle at which a magnetic head tape is wound around the rotating magnetic head device;

means for measuring the rate of wear of the magnetic head in response to an output produced from the magnetic sensor; and means for detecting a position of rotation of the rotating magnetic head device and supplying its detected output to the measuring means; and wherein the measuring means measures the rate of wear of the magnetic head, based on a variation in oscillating frequency of the magnetic sensor.

The magnetic sensor is disposed at and fixed to a position which falls outside a tape lap angle. The magnetic sensor comprises an inverted U-shaped frame core and a detecting coil wound in a winding groove defined in the core.

The width of the winding groove is wider than a gap width of the magnetic head and is narrower than the width of the magnetic head.

Since the total value of magnetic resistance including a plurality of magnetic heads and a magnetic sensor at rotational positions where the magnetic heads are respectively opposed to the magnetic sensor, changes as the magnetic heads wear out, a variation in magnetic resistance is taken as a variation in inductance. Since the inductance is a part of oscillator circuit elements, the oscillating frequency thereof also changes with the variation in inductance. Since the rate of wear of each magnetic head and the change in oscillating frequency are correlated with each other, an oscillating frequency at the time the rate of head wear is zero (before the magnetic head is used), is stored. If a variation in the subsequent oscillating frequency is monitored, then the rate of head wear at the time of its measurement can be recognized. When the rate of wear of the head exceeds a predetermined wear rate (predetermined value), a warning is issued to a user. This can avoid beforehand an undesired state that a signal is not suddenly recorded during recording of the signal.

Each position (address) to be measured relative to the magnetic head is shifted little by little. Further, an oscillating frequency is determined each time its shift is made, and positions where the magnetic sensor and the magnetic head are completely opposed to each other, are determined from total data thereof. Thereafter, the position to be measured is specified according to the corresponding addresses indicative of the completely opposed positions and its measurement is executed.

When the plurality of magnetic heads are provided with steplike offsets defined relative to each other in the direction of rotation of the rotating magnetic head device, the size (thickness) of the magnetic sensor is selected so that a single magnetic sensor can cover the magnetic heads, i.e., the plurality of magnetic heads are all included within a magnetic gap of the magnetic sensor.

The above and other objects, features and advantages of the present invention will become apparent from the following description and the appended claims, taken in conjunction with the accompanying drawings in which preferred embodiments of the present invention are shown by way of illustrative example.

BRIEF DESCRIPTION OF THE DRAWINGS

While the specification concludes with claims particularly pointing out and distinctly claiming the subject matter which is regarded as the invention, it is believed that the invention, the objects, features and advantages thereof will be better understood from the following description taken in connection with the accompanying drawings in which:

FIG. 2 is a configurational view illustrating one example of a rotating magnetic head device;

FIG. 3 is a configurational view showing another example of the rotating magnetic head device;

FIGS. 4(A) to 4(C) are view depicting the structure of a magnetic head to be measured;

FIG. 5 is an equivalent magnetic circuit diagram including a magnetic head and a magnetic sensor;

FIG. 6 is a systematic diagram showing one embodiment of a noncontact type magnetic head wear-rate measuring apparatus according to the present invention;

FIG. 7 is an equivalent configurational diagram of a variable oscillator circuit;

FIGS. 8(A) to 8(E) are explanatory diagram showing measured examples of the rates of head wear;

FIG. 9 is a curve diagram showing the relationship between the rate of head wear and an oscillating frequency;

DETAILED DESCRIPTION OF THE PREFERRED EMBODIMENTS

One embodiment of a noncontact type magnetic head wear-rate measuring apparatus according to the present invention, which is applied to a rotating drum device mounted to the above-described VTR, will hereinafter be described in detail with reference to the accompanying drawings.

Figure 1:
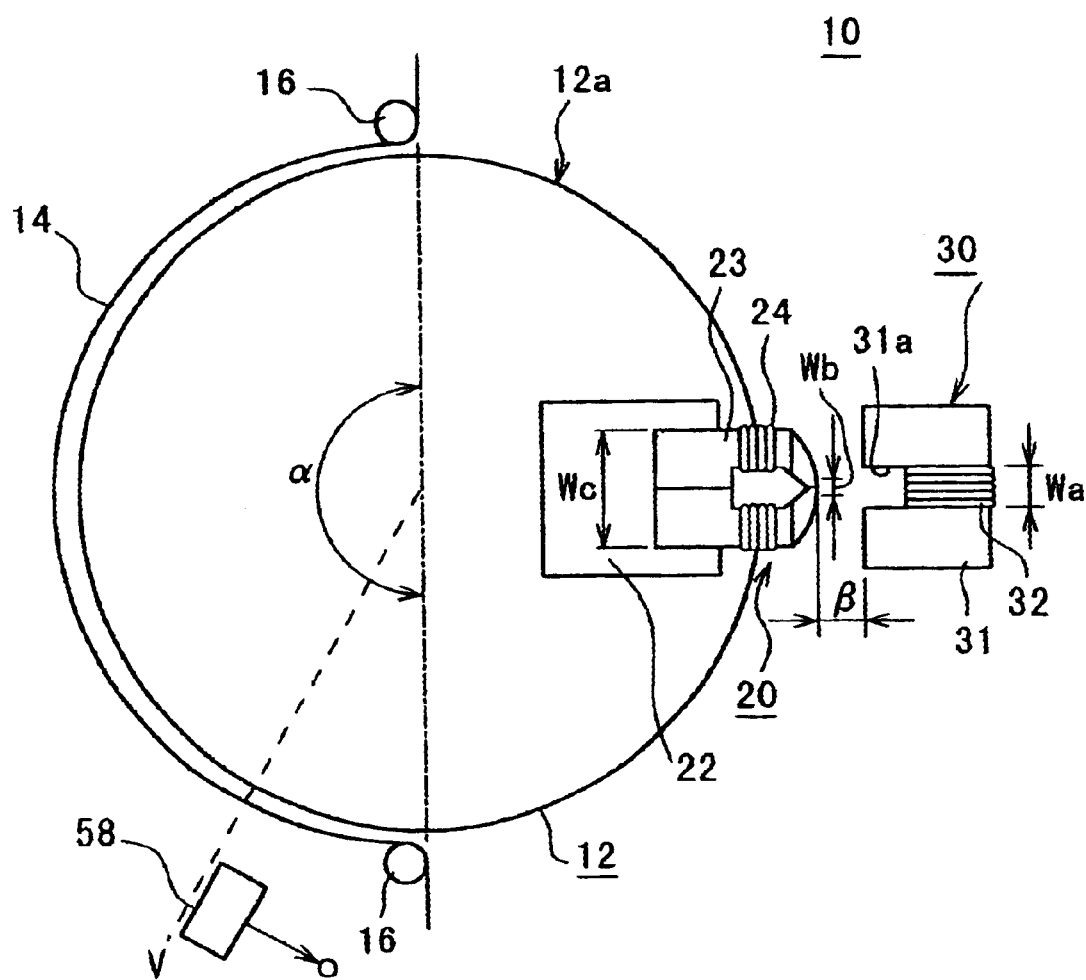
FIG. 1 is a conceptual view showing a summary of a noncontact type magnetic head wear-rate measuring apparatus according to the present invention.

FIG. 1 is a conceptual view showing a part of a noncontact type magnetic head wear-rate measuring apparatus 10 to which the present invention is applied. In a rotating magnetic head device 12, a magnetic tape 14 is helically wound around a surface 12a at a predetermined lap angle α defined by guide pins 16. Further, information is recorded on the magnetic tape 14 by a magnetic head 20 mounted to the rotating magnetic head device 12 and is reproduced or played back by the magnetic head 20.

A base 22 is placed in a predetermined position of the rotating magnetic head device 12. The magnetic head 20 is placed on and fixed to the base 22. The magnetic head 20 is mounted to the base 22 in a state of being projected from the surface of the rotating drum by a predetermined value or length. Signal windings 24 are respectively wound around both legs of a head core 23.

A magnetic sensor 30 is disposed in a position which is spaced at a predetermined clearance β from a magnetic head 20 of the rotating magnetic head device 12, specifically, a sliding surface of the magnetic head 20 and which does not fall within the tape lap angle α, e.g., an angular position away by 90° from the guide pins 16 when the lap angle α is about 180° as shown in the drawing. The magnetic sensor 30 comprises an inverted U-shaped frame core 31 and a detecting coil 32 wound in a winding groove 31a defined in the core 31. The detecting coil 32 wound around the magnetic sensor 30 serves as a part of oscillating elements of a variable oscillating circuit (OSC) to be described later.

When the rotating drum device is constructed such that a lower drum 33 thereof is fixed and only an upper drum 34 is rotated as shown in FIG. 2, the upper drum 34 also functions as the rotating magnetic head device 12. At this time, the above-described magnetic sensor 30 is mounted and fixed to a mounting member 38 having an L-shaped cross section, which is attached to the lower drum 33, so as to be opposed to the magnetic head 20 of the upper drum 34.

On the other hand, when a rotating drum device having an intermediate drum (rotating drum) 36 and constructed such that a magnetic head 20 is mounted to the intermediate drum 36 and upper and lower drums 33 and 34 thereof are fixed to the intermediate drum 36,is used, a magnetic sensor 30 is mounted and fixed to an inverted U-shaped mounting member 38 provided across the upper and lower drums 33 and 34.

The magnetic head 20 is composed of a pair of cores 23 and signal windings 24 as shown in FIG. 4(A). FIGS. 4(B) and 4(C) are respectively cross-sectional views as seen from the direction indicated by arrow D (not shown) in FIG. 4(A). A tape sliding portion 25 including a tape sliding surface 25a is configured in a cut-away form as shown in FIG. 4(B). Each of the cores 23 may be a single-layered core composed of only a magnetic substance or material as illustrated in FIG. 4(B). Alternately, the core 23 may be a layered core in which a metal 23b is placed at the intermediate portion and non-magnetic materials (ceramic) are placed in positions above and below the metal 23b as shown in FIG. 4(C).

Since the magnetic head 20 is rotating, two states: one in which the magnetic head 20 is in an opposing relationship to the magnetic sensor 30 during one turn or rotation and the other in which the magnetic head 20 is in a non-opposing relationship to the magnetic sensor 30, are produced. When the magnetic head 20 is in a state of being opposed to the magnetic sensor 30 as shown in FIG. 1, a magnetic circuit composed of the magnetic head 20 and the magnetic sensor 30 can be represented in the form of an equivalent circuit shown in FIG. 5.

In the equivalent circuit illustrated in FIG. 5, symbol Ra indicates a magnetic resistance of the tape sliding portion 25 and symbol Rb indicates a magnetic resistance of a back core (core 23 other than the head sliding portion 25). Similarly, the resistance of the detecting coil 32 of the magnetic sensor 30 is designated at symbol Rc. Further, magnetic resistance in a magnetic gap 36 at the time that the two are opposed to each other, are respectively represented as Rd and Re. Here, the magnetic resistance Rd and Re respectively correspond to magnetic resistance between both legs of the inverted U-shaped frame core 31 and the tape sliding portion 25.

Since the thickness of the tape sliding portion 25 decreases when the tape sliding portion 25 wears out, the magnetic resistance Ra changes. Simultaneously, since the opposed space or clearance between the tape sliding portion 25 and the magnetic sensor 30 also changes, the magnetic resistance Rd and Re also vary correspondingly. Thus, the total value of the magnetic resistance as viewed toward the magnetic head 20 from the magnetic sensor 30, is changed due to the wearing away of the magnetic head 20.

FIG. 6 is a diagram showing the summary of a circuit system of a noncontact type magnetic head wear-rate measuring apparatus 10 according to the present invention. A change in inductance due to the variation in magnetic resistance shown in FIG. 5 is introduced into a variable oscillator circuit 40. The variable oscillator circuit 40 has an amplifying stage 42 composed of transistors corresponding to amplifying elements for oscillation as shown in FIG. 7. In the present embodiment, LC elements are electrically connected to a parallel feedback path corresponding to the amplifying stage 42 as oscillating elements. The LC elements are a capacitor 44 corresponding to a capacitative element and a variable inductance element 46 electrically connected in parallel to the capacitor 44. The variable inductance element 46 indicates the total inductance Lx shown in FIG. 5.

When the inductance Lx varies, the oscillating frequency changes correspondingly. The oscillated output is introduced into a digital measuring circuit 50 where it is converted into a counted value proportional to the frequency. Its details will be described later. A count output corresponding to the oscillating frequency is supplied to a wear-rate calculating means 52 provided at a subsequent stage.

A CPU is provided within the wear-rate calculating means 52 and calculates the rate of wear of the magnetic head 20 based on the resultant measured data. Data about the calculated wear rate or the like is stored in a memory 54 and supplied to a display means 56 to display the calculated value or the like thereon.

When the wear rate has reached a predetermined value or more, a notifying means (not shown) such as a warning means or the like may be activated aside from this process to inform a user that "there is a possibility that information cannot be recorded properly if such a head is left as it is and the head must be immediately replaced by another". The predetermined value can be selected to a value immediately before, for example, a head depth (see 25b in FIG. 4(A)) vanishes or disappears. When the head depth is about 25μ, for example, 20μ or so can be selected as the predetermined value.

The above-described measuring process can be performed immediately after the power for the measuring apparatus has been turned on, for example. It has been understood from practical experience that when the magnetic head is normally used over a period of 500 to 1000 hours, it wears to several tens of microns, thus resulting in interference with recording and reproduction. Therefore, software may be constructed so that the measuring process is executed from the time immediately before such service time with the service time as a guide. The value of a recording current is controlled so as to be reduced with an increase in wear rate, aside from the measuring process and a magnetic head may be replaced by another only when the limit wear rate (corresponding to a value near the head depth) is detected.

The rate of head wear can be measured over the entire periphery of the drum. Alternatively, the wear rate may be measured only during a section or interval in which the magnetic head 20 and the magnetic sensor 30 confront each other. As shown in FIG. 1, a revolution detecting means (such as a pulse generator PG) 58 is provided on a direct extension of a radius which passes through the center of rotation of the drum. An angular position of rotation of the drum is detected on the basis of one PG pulse per turn or revolution of the drum, which is obtained from the revolution detecting means. Thus, the timing provided to measure the wear rate of the magnetic head by the magnetic sensor 30 can be determined. This is because the relationship between the timing provided to obtain the PG pulse and the position of mounting of the magnetic head 20 to the drum is known and the relative positional relationship between the two is apparent in advance.

As shown in FIG. 1, a width Wa of the winding groove 31a defined in the core 31 that constitutes the aforementioned magnetic sensor 30, is selected so as to be greater than a width Wb of a gap g of the magnetic head 20 and narrower than a width Wc of the magnetic head 20 itself. This is made to create a magnetic gap between the magnetic sensor 30 and the magnetic head 20 as mentioned above and change the value of each of the magnetic resistance formed by the magnetic head 20 and the magnetic sensor 30 according to the wear of the sliding surface 25a of the magnetic head 20. Examples of specific values of these will be mentioned as follows:

Wa=250 μm, Wb=0.5 μm and Wc=1.5 mm

This is because when the width Wa of the winding groove 31a is narrower than the width Wb of the gap g of the magnetic head 20 (such a configuration is impossible in practice) and is broader than the width Wc of the magnetic head 20 itself, the rate of wear of the magnetic head 20 cannot be accurately taken as a change in magnetic resistance. Since the opposite clearance β exerts an influence on detection sensitivity, the optimum clearance value is selected.

When the magnetic sensor 30 is used and the wear rate of the head is measured according to the change in magnetic resistance thereof as in the present invention, a high-accuracy wear rate measurement can be realized by simply making a fine adjustment to the mounting position of the head so that the opposite clearance β is set according to the designed value. According to experiments, it has been confirmed that the head wear rate can be measured (and predicted) with an accuracy of ±1 μm. It has also been confirmed that in the case of a magnetic head using a layered core in particular, the rate of wear of the magnetic head can be measured with an accuracy of ±0 μm. Since the magnetic sensor 30 itself is a microminiaturized element and those other than it are circuit parts, the scale of the measuring apparatus becomes so small.

Digital processing may be presented by the aforementioned measuring circuit 50. That is, the measuring circuit 50 is coupled to a reference clock source or oscillator (OSC) 68, which may generate a plurality of reference clock pulses CK, and may perform digital processing based on the reference clock pulses CK obtained from the reference clock source 68 as shown in FIG. 6.

Meanwhile, the rate of wear of the magnetic head 20 may be theoretically calculated from only one measurement thereof at the position where the magnetic sensor 30 is completely opposed to the magnetic head 20. However, this cannot achieve the calculation of the rate of head wear with satisfactory accuracy.

Therefore, measurement start positions are respectively measured only for a predetermined time interval while being successively shifted during a period in which the magnetic head 20 starts to approach the magnetic sensor 30 and is separated from the magnetic sensor 30. Thereafter, the rate of head wear at the completely opposed position may be calculated from those measured data.

For example, a region corresponding to one rotation of the drum is divided into n, and thereafter the rate of head wear may be calculated based on measured data in the divided region of the n-divided regions, which is lying in a peripheral region in which the magnetic head 20 is actually opposed to the magnetic sensor 30.

FIGS. 8(A) through 8(E) respectively show conceptual views of examples of the measured rates of head wear. Since a position P of mounting of the magnetic head 20 to the pulse generator (PG) 58 is known in advance, addresses are given to n-divided angular positions of rotation of the drum with the mounting position of the pulse generator 58 as a reference point. The number of addresses will increase in a counterclockwise direction in the embodiment illustrated in FIG. 6.

By integrating a predetermined number of oscillating frequency waveforms lying within a pre-set measurement time T from the initial measurement start address A1 as shown in FIG. 8(B), an oscillating frequency f1 at the measurement start address A1 (corresponding to the medium value of an address number lying within T in practice) is obtained.

Similarly, the measurement start address is shifted to A2 (>A1) as shown in FIG. 8(C) upon the next rotation to execute the same measurement as described above, whereby an oscillating frequency f2 at this time is determined. Measuring processes are successively executed up to the final measurement start address (A7 in the present example) while the measurement start addresses A are being successively shifted, whereby oscillating frequencies f3 through f7 at the respective measurement start addresses A3 through A7 are determined. The respective frequencies f are finally converted into numeric values (measured data) Y1 through Y7 respectively.

The position where the magnetic head 20 is completely opposed to the magnetic sensor 30, becomes narrowest as the opposite clearance β and the frequency at this time results in the lowest frequency. Since the oscillating frequency f increases as the opposite clearance β expands, a characteristic curve La shown in FIG. 9 is obtained in practice.

Figure 10A:
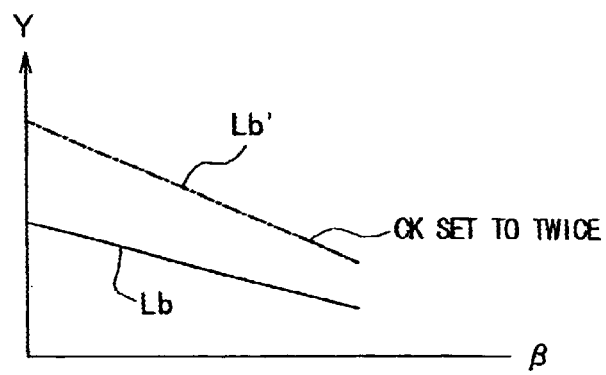
FIGS. 10(A) and 10(B) are characteristic diagram illustrating the relationship between an opposite interval and measured data.

FIG. 10(A) shows the relationship between the opposite clearance β, i.e., the oscillating frequency f and measured data Y at that time. As will be described later in the illustrated example, the measured data Y is reduced as the oscillating frequency f increases and thus the opposite clearance β becomes great. Therefore, the measured data Y increases up to the measurement start address A at which the opposite clearance β is minimized. Thus, if the relationship between the measurement start address A and the measured data Y at that time is represented in diagrammatic form, then a single crest characteristic brought into convex form upward as shown in FIG. 11 is given.

Figure 11:
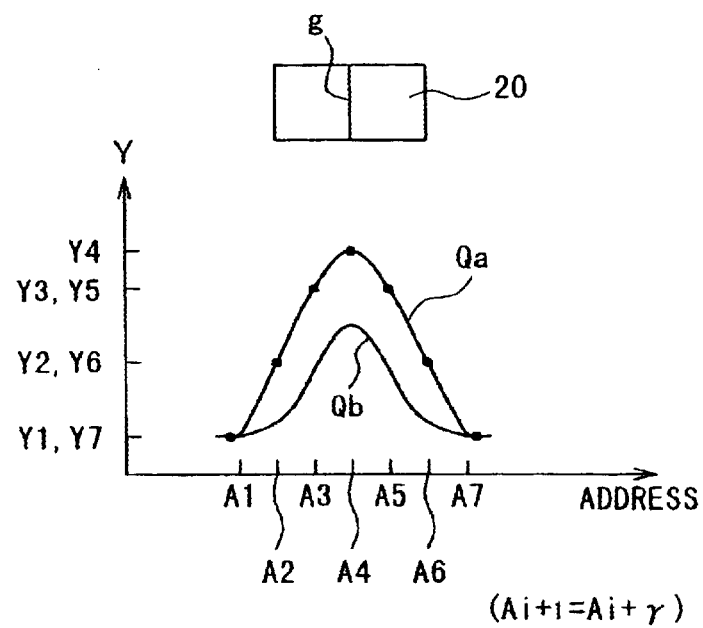
FIG. 11 is a characteristic diagram depicting the relations of measured data.

Since the maximum value corresponds to the position of a gap g, the rate of head wear is measured at a stage prior to the use of the magnetic head 20 and a measured value (corresponding to a reference value, which will be defined as a curve Qa shown in FIG. 11) at this time is stored. Since a head confronting or facing surface 25a (see FIG. 4(A)) wears out as the magnetic head 20 is used, the opposite clearance β becomes wider than that prior to the use of the head. As the opposite clearance β becomes large, the oscillating frequency f increases and correspondingly the measure data Y is reduced. Thus, when the rate of head wear is measured after the magnetic head 20 is used to some extent, its measured value is represented as a curve Qb shown in FIG. 11. When the difference between the maximum values of respective measured data has reached a reference value or more, the magnetic head is brought to the time to be replaced by another.

Figure 12:
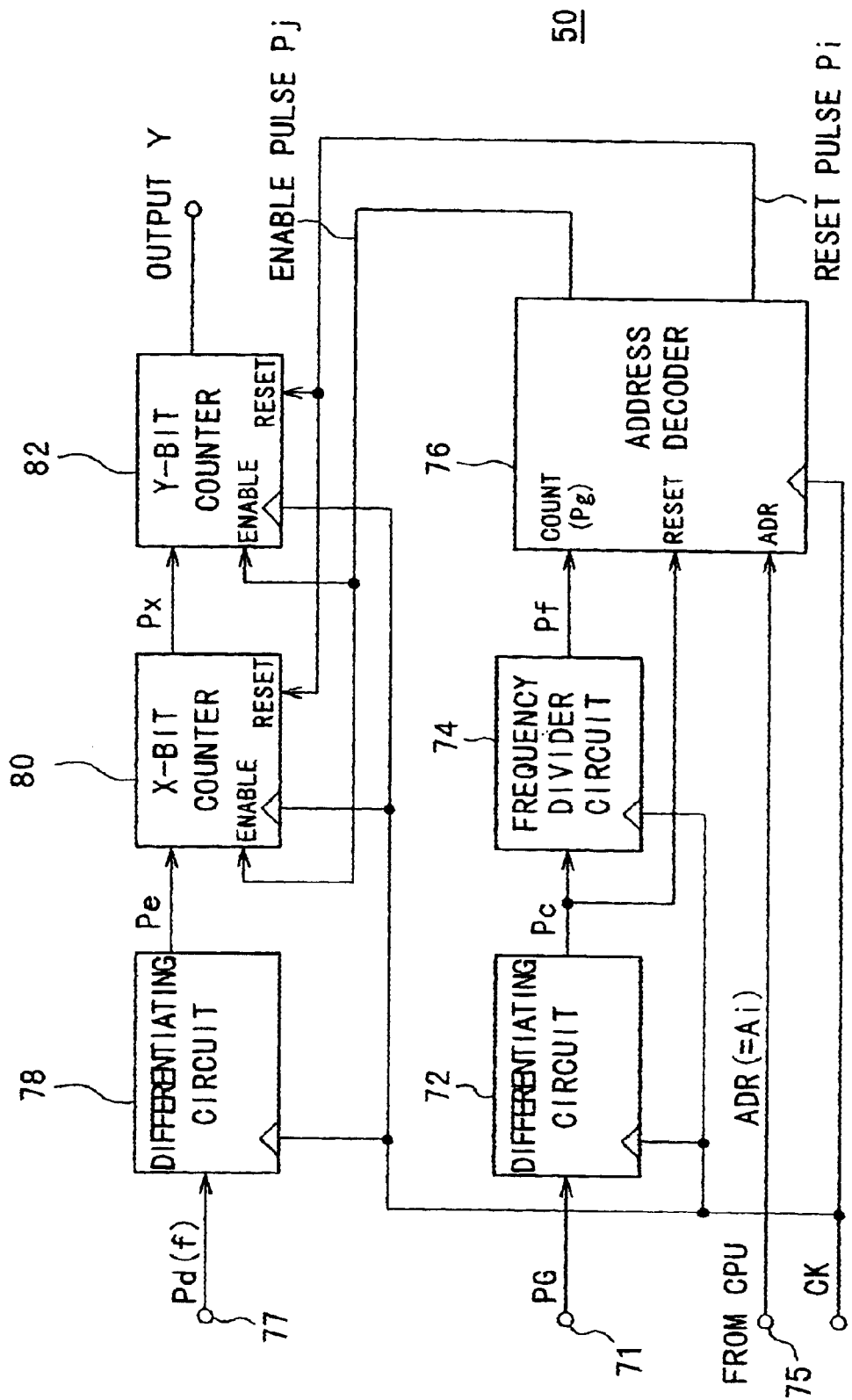
FIG. 12 is a systematic diagram showing a specific example of a digital measuring circuit.

The above-described measuring process is performed in the aforementioned digital measuring circuit 50. FIG. 12 is a specific example of the digital measuring circuit 50.

Figure 13:
FIGS. 13(A) to 13(L) are waveform diagram (part 1) illustrating an example of measurement of the rate of wear of a digital type head.

A terminal 77 is first supplied with a measurement signal Pd (see FIG. 13(D)) produced by bringing the oscillating frequency f at the measurement interval T, which is obtained from the variable oscillator circuit 40, into digital form. The measurement signal Pd is differentiated by a differentiating circuit 78 to obtain a measurement differential pulse Pe shown in FIG. 13(E). The cycle of the measurement differential pulse Pe depends on the measured oscillating frequency f. Since the measured oscillating frequency slightly varies according to the value of the opposite clearance β, a pulse cycle thereof will expand and contract little by little as shown in the drawing.

The measurement differential pulse Pe is supplied to a first counter 80 corresponding to the following stage, where it continues counting until the value of the counter reaches a predetermined count value (e.g., YY bit). The first counter 80 is made up of an x-bit (>YY bit) counter. The output of the first counter 80 is brought to a high level according to its count start. Thus, a pulse signal inverted to a low level when the count value reaches the YY bit, is obtained.

The first counter 80 has a count enable period corresponding to a period enough to be able to count the YY bit even when the frequency is lowest during a measurement mode. An enable signal (pulse) Pj (see FIG. 13(J)) for defining the count enable period is produced by the following means.

A PG pulse (see FIG. 13(B)) inputted to a terminal 71 is supplied to a differentiating circuit 72 where a PC differential pulse Pc synchronized with a clock CK (see FIG. 13(A)) is produced as shown in FIG. 13(C). The PG differential pulse Pc is supplied to a 1/n (where n: arbitrary integer) frequency divider circuit 74.

Since the frequency divider circuit 74 is supplied with the clock CK generated from the oscillator 68, one frequency-divided pulse Pf (see FIG. 13(F)) is outputted each time the clock CK is counted by n. Since the frequency of the clock CK is constant, the period or cycle Tf of the frequency-divided pulse Pf is also constant. m frequency-divided pulses Pf are obtained per turn of the drum by selecting a division ratio n to a suitable value. Thus, one turn of the drum is divided into 1/m.

Thus, since the magnetic head 20 is located at a position advanced by r (where r: arbitrary integer) with the PG pulse as the reference, the present frequency-divided pulses Pf can be used as drum's addresses.

Each frequency-divided pulse Pf is supplied to an address counter 76 corresponding to the following stage from which an address is supplied for each pulse of the frequency-divided pulses Pf (see FIG. 13(G)). The address counter 76 is supplied with the PG differential pulse Pc as a reset pulse. In addition to this pulse, a measurement start address ADR (=Ai) (see FIG. 13(H)) is specified to the address counter 76 through a terminal 75. An example illustrated in FIGS. 13(A) through 13(L) shows an example in which an initial measurement start address A1 is supplied to the address counter 76. In the illustrated example, A1="08H" (where H: hexadecimal representation) is given as A1.

When address data related to the frequency-divided pulse Pf coincides with the measurement start address A1, a reset pulse Pi (see FIG. 13(I)) is obtained from the address counter 76 and an enable pulse Pj (see FIG. 13(J)) which rises for a predetermined period T alone according to the reset of the reset pulse Pi, is produced.

The enable pulse Pj is a pulse for defining a measurement period T and these pulses Pi and Pj are respectively supplied to the first counter 80 as the reset pulse and the enable pulse as described above. Thus, the first counter 80 is reset immediately before the commencement of measurement and the number of measurement differential pulses Pe inputted during a period in which the enable pulse Pj is high in level, is counted by the first counter 80. When the counted value reaches a predetermined number (=YY bit), an X-bit counter output Px (see FIG. 13(K)) corresponding to the output of the first counter 80 is inverted to a low level.

The interval of each measurement differential pulse Pe corresponds to the cycle of a measured oscillating frequency. Since the pulse interval becomes wide when the frequency thereof is low (β is narrow), a time interval WT (see FIG. 13(K)) necessary for the X-bit counter output to reach the YY bit becomes long.

On the other hand, when the measured oscillating frequency is high (β is wide), the pulse interval becomes narrow and hence the time interval WT required to count the counter output up to the YY bit becomes short. Thus, the X-bit counter output Px results in a pulse-width modulated pulse output, which is supplied to a second counter 82.

The second counter 82 resets the contents thereof in response to the aforementioned reset pulse Pi and enters into a count mode only during a period of the X-bit counter output Px inputted during the enable pulse Pj to thereby count up the clock CK (see FIG. 13(L)).

Thus, when the measured oscillating frequency is low and consequently the pulse width of the X-bit counter output Px is wide (see FIGS. 14(A) through 14(D)), a counter output (corresponding to a Y-bit counter output Py) Y produced from the second counter 82 reaches a large value correspondingly.

Figure 14:
FIGS. 14(A) to 14(G) are waveform diagram (part 2) showing an example of measurement of the rate of wear of the digital type head.

On the other hand, when the measured oscillating frequency is high and consequently a pulse width of an X-bit counter output Px is narrow as shown in FIGS. 14(E) through 14(G), measured data Y corresponding to a Y-bit counter output takes a small value correspondingly.

Thus, the result of measurement shown in FIG. 11 is obtained. As the magnetic head 20 wears out with its use, the opposite clearance β gradually expands even though its expansion is extremely slight. Therefore, a characteristic about measured data Y at this time is represented like the curve Qb shown in FIG. 11. When the rate of head wear is measured at a stage prior to the use of the magnetic head 20 to thereby obtain the result of measurement represented by the curve Qa shown in FIG. 11, and the rate of head wear is next measured while the magnetic head 20 is in use, to thereby obtain the result of measurement represented by the curve Qb shown in FIG. 11, the difference between their peak values is compared with a predetermined value to thereby determine the rate of head wear.

A curve Lb shown in FIG. 10(A) shows the relationship between the opposite clearance β and the measure data Y. If the frequency of the clock CK is now increased in a state in which the number of revolutions of the drum is kept constant, then the number of pulses countable during the pulse width of the X-bit counter output Px increases. Thus, since the measured data Y increases, the relationship therebetween at that time is represented like a curve Lb' indicated by a chain line in FIG. 10(A), whereby measuring accuracy is improved.

Figure 10B:
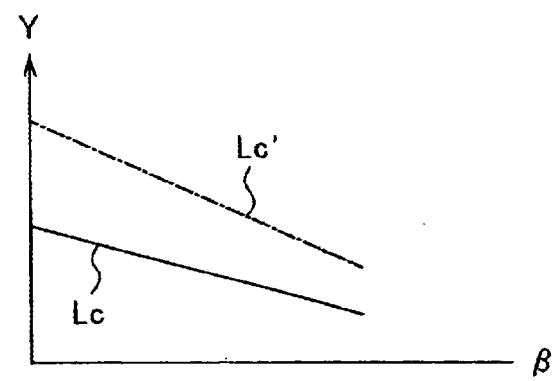

Similarly, when the rotational frequency of the drum is lowered to ½, for example in a state in which the frequency of the clock CK is held constant, the measurement period T itself is expanded twice, thus leading to the same result as when the frequency of the clock is increased. Namely, since the number of pulses countable within the measurement period T is increased twice, the measuring accuracy is improved to twice correspondingly as represented by a curve Lc' indicated by a chain line in FIG. 10(B).

Figure 15:
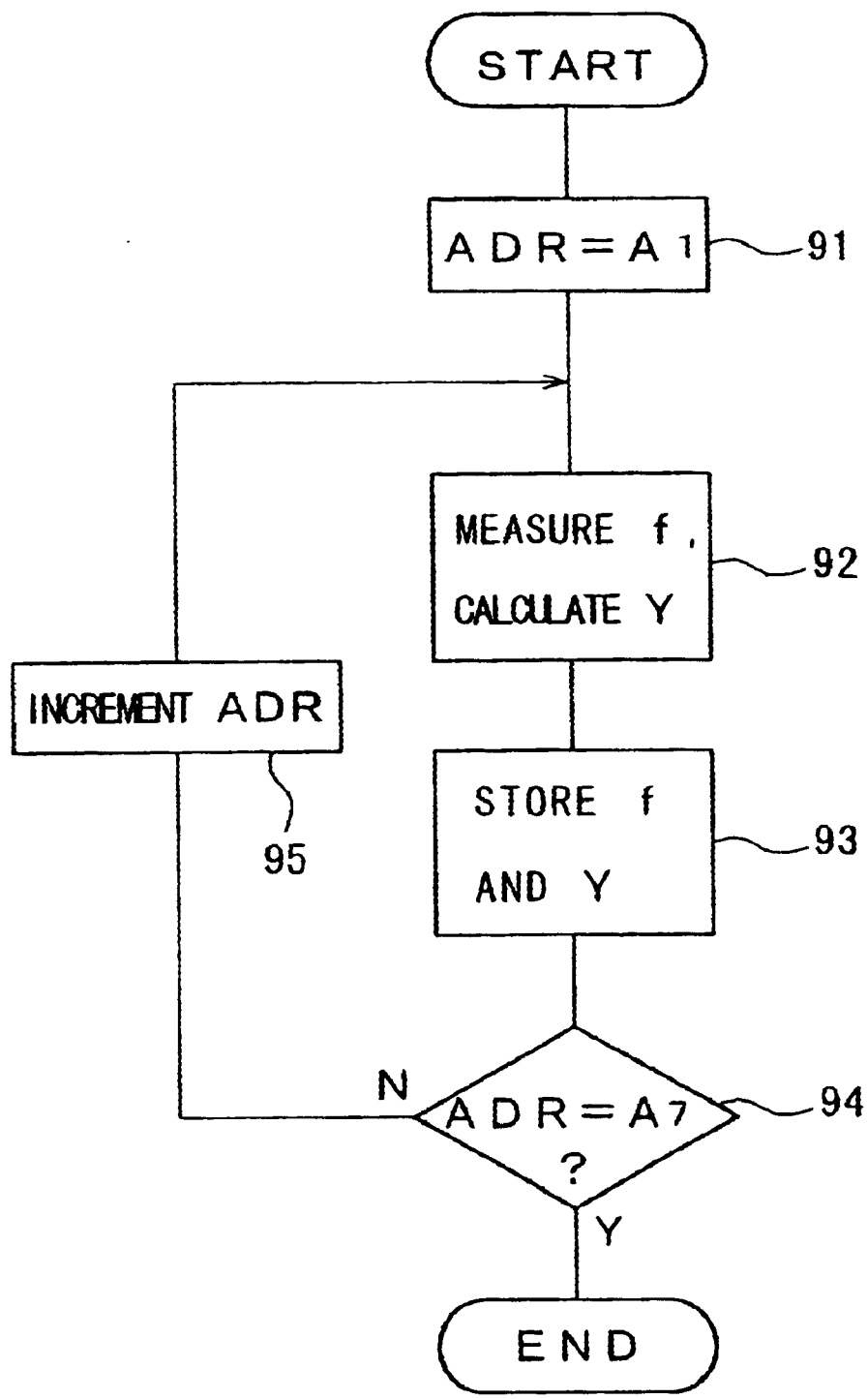
FIG. 15 is a diagram showing a measuring flowchart for calculating an initial value of the rate of head wear.

FIG. 15 is a flowchart showing an example of a measuring process for measuring an initial value of the aforementioned rate of head wear and shows an example of a process for shifting the measurement start position seven times as described above to thereby allow the measurement of the rate of wear of the magnetic head 20.

A measurement start address ADR is first initialized (Step 91). In the present example, the measurement start address ADR is set to an initial address A1. An oscillating frequency f obtained during a predetermined period T from the measurement start address A1 is integrated (Step 92). Measured data Y (=Y1) on the integrated oscillating frequency f is calculated. At least the measured data Y is stored and the oscillating frequency f is stored as needed in addition to the measured data Y (Step 93).

Upon the rotation of the drum subsequent to the second time, the measurement start address ADR is sequentially incremented by 1 (Steps 94 and 95). Similar processing is executed up to a measurement start address A7. The measuring process for calculating the initial value of the rate of head wear is terminated at a stage in which the measuring process at the measurement start address A7 is completed.

Of these seven measured data Y1 through Y7, measured data used when the actual rate of head wear is detected and the presence or absence of the replacement of the head by another is determined, include only a plurality of measured data lying before and behind the peak value with the peak value interposed therebetween. In the present example, Y3, Y4 and Y5 may be mentioned as such measured data. For example, the mean value thereof is used as initial value data (reference data).

Thus, the measuring processing is executed by specifying only the three addresses as the measurement start addresses used when the rate of head wear is calculated. An example of a process for providing head replacement instructions at that time is illustrated in FIG. 16.

Figure 16:
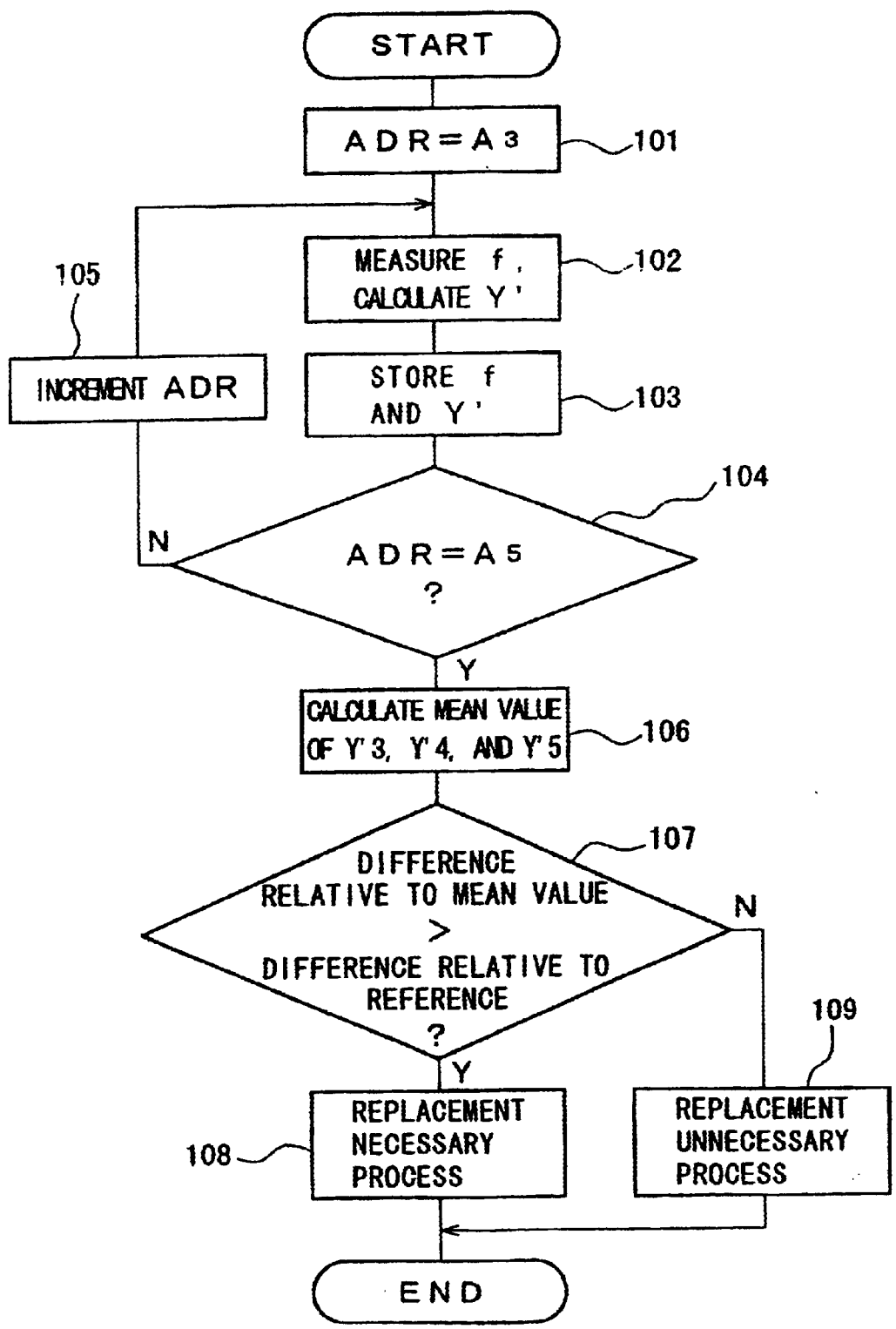
FIG. 16 is a diagram depicting a head replacement processing flowchart.

Since an address initial value changes from A1 to A3 during Steps 101 through 105 and a decision address in Step 104 simply changes from A7 to A5 in FIG. 16, their detailed description will be omitted.

The mean value of measured data Y3', Y4' and Y5' obtained in the aforementioned process is calculated in Step 106 and the difference between the already-stored initial value data (reference data) and the calculated average or mean value is determined (Step 107). When the difference is smaller than the reference value, the magnetic head 20 wears out but is determined not to lead to its replacement (Step 109).

On the other hand, when the difference is found to be equal to or greater than the reference value, the magnetic head 20 is judged to have reached the time to be replaced by another (Step 108). At this time, a message indicative of the contents of its replacement time is displayed on a displayer (not shown), a warning lamp is caused to blink or its contents is notified to a user by voice to thereby urge the user to replace the magnetic head by another.

In the present invention as described above, the rotational position detecting means 58 for detecting a rotational reference position of the rotating drum is provided. The detected pulse obtained from the rotational position detecting means 58 is supplied to the digital measuring circuit 50 from which the frequency-divided pulses Pe for dividing one turn or rotation of the drum into n are determined, whereby an address for the position to mount the magnetic head 20 to the drum as viewed from the rotational reference position is determined. The measurement start address ADR is specified while the address is being shifted in sequence.

Therefore, the digital measuring circuit 50 is provided with the first and second counters 80 and 82. The train of pulses Pd of the measured oscillating frequency is supplied to the first counter 80 from which the pulse (counter output) Px having the pulse width up to the counting of a predetermined number of pulses is generated.

Further, the counter output Px is supplied to the second counter 82 where the number of reference clocks lying within the pulse width is counted. This counter output Py is used as the measured data Y corresponding to the opposite clearance between the magnetic sensor 30 and the magnetic head 20.

Now, the magnetic head 20 mounted to the rotating magnetic head device 12 shown in FIG. 1 is illustrated as single for convenience of illustration. It is a general rule that several magnetic heads 20 are practically disposed with specific intervals held with respect to the direction of rotation thereof. Thus, even when the rate of wear of each head is measured in the case of the provision of the plurality of magnetic heads, the usage of a single magnetic sensor as the magnetic sensor would be wiser from the viewpoint of measuring accuracy and construction.

Figure 17:
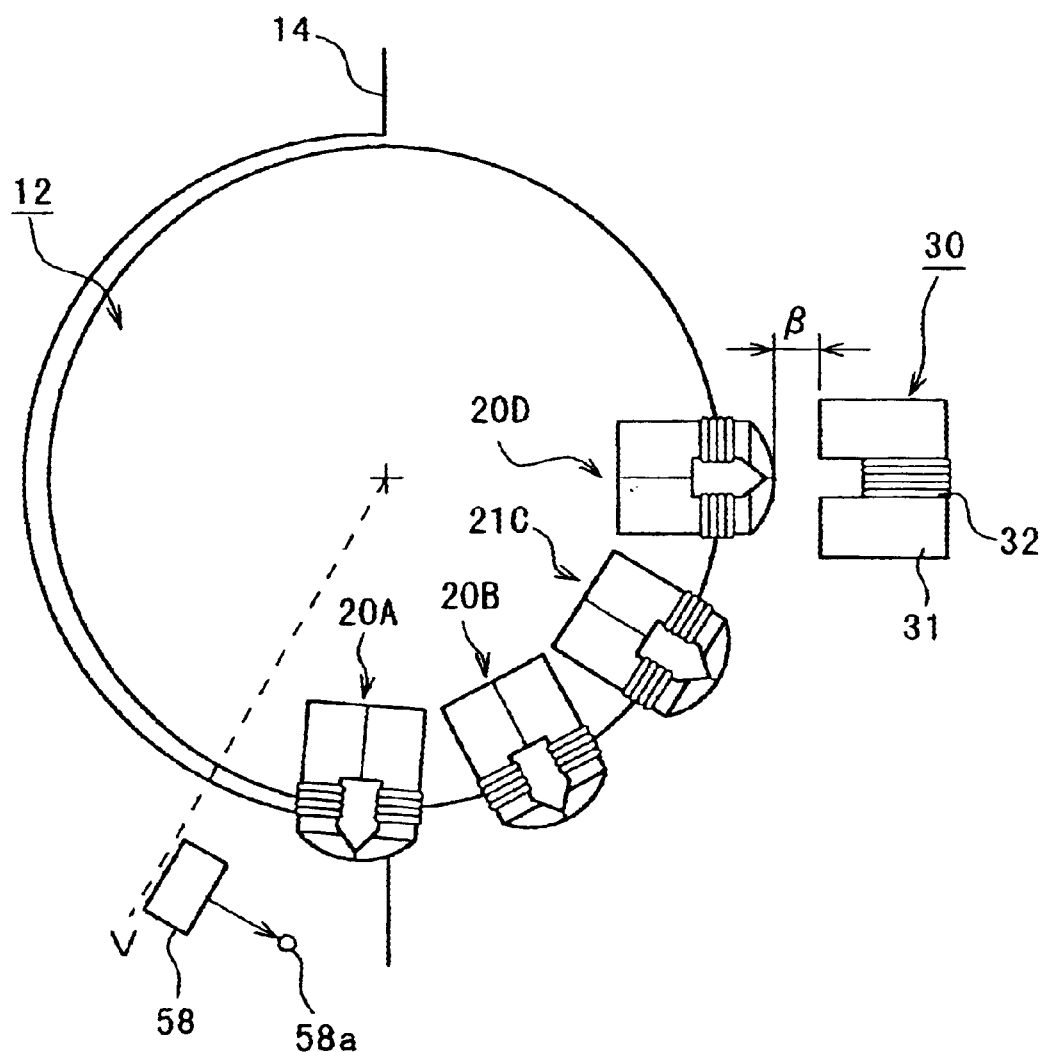
FIG. 17 is a view showing the same concept as that shown in FIG. 1 at the time that a plurality of magnetic heads are used.
Figure 18:
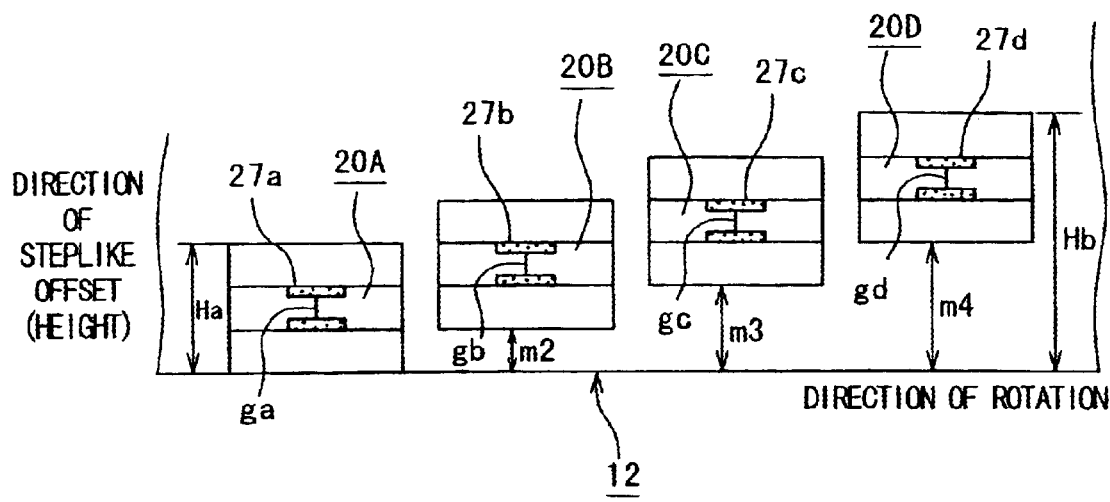
FIG. 18 is a view illustrating the magnetic heads shown in FIG. 17 in a developed form.

FIG. 17 is a conceptual view of a measuring apparatus 10 constructed in consideration of such a point. The illustrated example shows one in which four magnetic heads 20A through 20D are disposed with predetermined steplike offsets defined relative to each other in the direction of rotation of a drum. If the end surface of the drum is considered as the reference, then the magnetic heads 20B, 20C and 20D identical in configuration to each other are disposed so as to have steplike offsets of m2, m3 and m4 with respect to the magnetic head 20A used as the reference as shown in FIG. 18. Symbols ga, gb, gc and gd respectively indicate gaps. Upper and lower ends of the gaps ga through gd are respectively filled with glass materials 27a through 27d as is already known.

Figure 19:
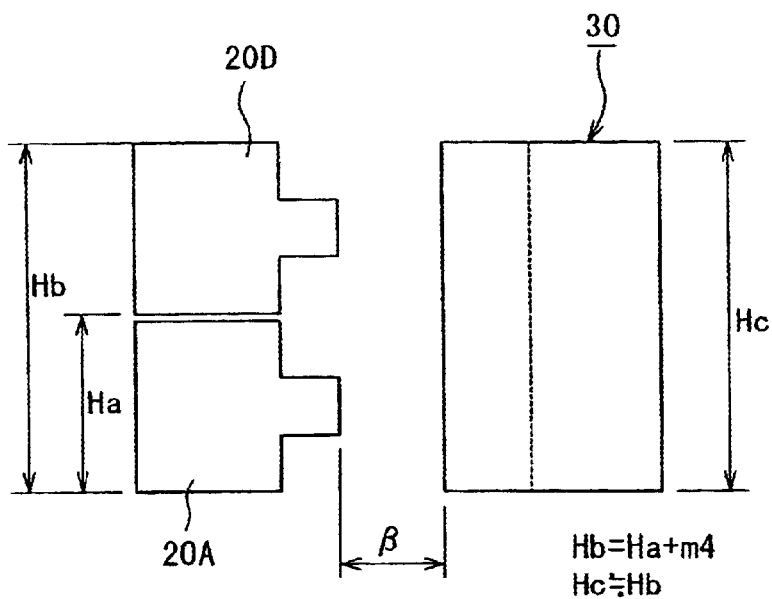
FIG. 19 is a layout as seen from the side of FIG. 17.

A magnetic sensor 30 disposed so as to be opposed to the plurality of magnetic heads 20 is constructed as shown in FIG. 19. If the thickness (extending in the axial direction of the rotating drum) of each magnetic head 20 is defined as Ha, then a thickness Hb between the magnetic heads 20A and 20D is given by the following equation:

$$Hb = Ha + m4$$

Thus, a thickness Hc of the magnetic sensor 30 is given by the following expression so as to be able to cover all the magnetic heads 20:

$$Hc \geq Hb$$

If done so, then the rates of wear of all the magnetic heads 20 can be measured by one magnetic sensor 30 alone. The above-described PG pulse is used to recognize whether the rates of wear of the magnetic heads 20 at any locations in space should be measured by the magnetic sensor 30. This is because the relationship in position between the timing provided to generate the PG pulse and each magnetic head is univocally decided.

When the thickness of the magnetic sensor 30 is selected to the aforementioned value Hc, it is considered that the magnetic resistance Rc and Rd of the magnetic spaces differ from each other according to the magnetic heads 20A through 20D to be measured and hence the measuring accuracy varies. However, there is practically little difference. This is because the magnetic resistance of the core 31 itself is considered to be small.

Figure 20:
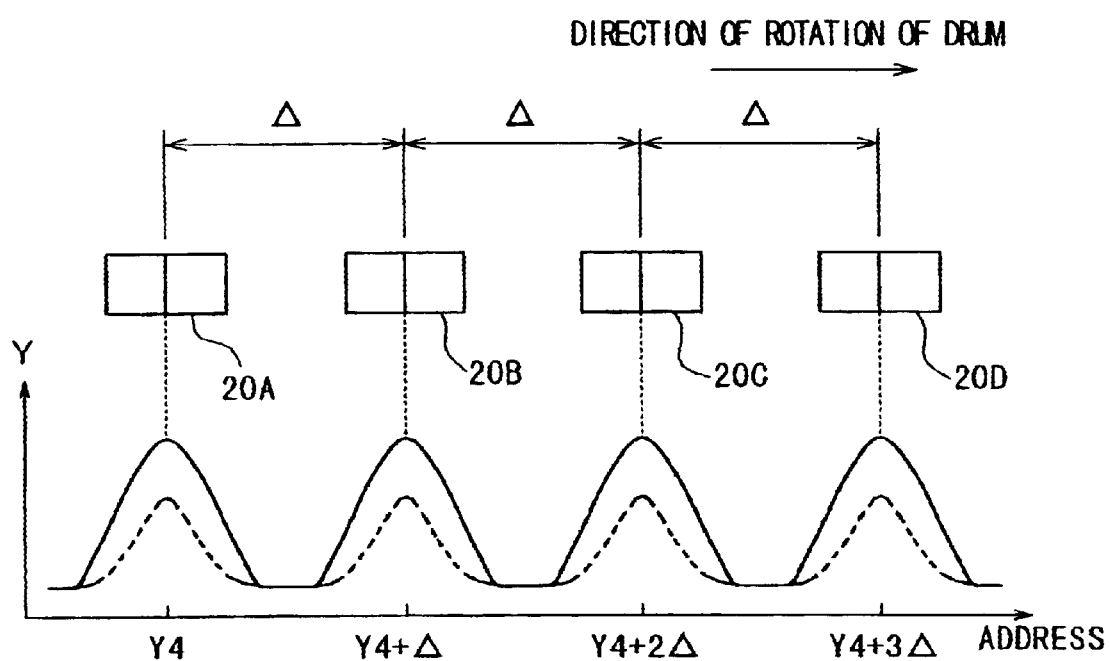
FIG. 20 is a diagram showing the relationship between a plurality of heads and the rates of wear of the heads.

In a manner similar to the measurement of the rate of head wear with respect to one magnetic head 20, the measurement start address A is shifted by $\Delta$, $2\Delta$ and $3\Delta$ respectively as shown in FIG. 20 even in the case of the plurality of magnetic heads 20A through 20D. As a result, reference data Qa1 through Qa4 with respect to the plurality of magnetic heads 20A through 20D and measured data Qb1 through Qb4 at the time of wear in heads are obtained.

It is apparent that if the apparatuses each having the rotating magnetic head are used as described above, then the present invention can be applied to all the head rate-of-wear measuring apparatuses. Although the magnetic sensor is used as single, two magnetic sensors may be used so that the difference between oscillating frequencies obtained from the two is measured and thereafter compared with a reference value to thereby determine the rate of head wear.

In the aforementioned noncontact type magnetic head rate-of-wear measuring apparatus, the magnetic sensor is disposed in a state of being in non-contact with the rotating magnetic head device. The degree of extension of the magnetic head from the drum surface, i.e., the rate of wear of the head can be measured by detecting the change in magnetic resistance of the magnetic circuit including the magnetic sensor.

According to the noncontact type magnetic head rate-of-wear measuring apparatus, it is possible to prevent a magnetic head to be measured from damage before it happens as compared with a contact type measuring apparatus using a contact or the like. Since the rate of wear of the head is measured according to a change in magnetic resistance unlike a noncontact type measuring apparatus using a laser beam or the like, measuring accuracy can be improved and the measuring apparatus itself can be reduced in size. Therefore, the measuring apparatus has a feature that it can be mounted to its mounting position without any restrictions. Thus, the measuring apparatus can be easily applied even to a rotating drum device whose drum diameter is small.

Since the rate of wear of the magnetic head is digitally measured only during the predetermined interval with the PG pulse as the reference, the measuring apparatus has a feature that it is high in measuring accuracy and can be reduced in circuit configuration too. If the rate of head wear is measured in a state in which the frequency of a clock to be used is increased and the number of revolutions of the drum is controlled to a low speed, then the number of clocks to be counted increases, thus leading to an improvement in measuring accuracy as a matter of course. As is to be appreciated to one of ordinary skill in the art, the clock frequency may be increased by utilizing a variable oscillator or a number of oscillators such as a number of OSCs 68 shown in FIG. 6.

Thus, the present invention is so suitable for use in AV devices such as a VTR, a DAT, a data recorder, etc.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is therefore contemplated that the appended claims will cover any such modifications or embodiments as fall within the true scope of the invention.

What is claimed is:

1. A noncontact type magnetic head wear-rate measuring apparatus, comprising:
   a magnetic sensor having an oscillating frequency and being opposed to a rotating magnetic head device with a magnetic head mounted thereon and disposed in a state placed in noncontact with the rotating magnetic head device so as to fall outside an angle at which a magnetic tape is wound around the rotating magnetic head device;
   means for generating reference clock pulses having a frequency associated therewith which is increasable;
   measuring means for processing an output produced from said magnetic sensor based on the generated reference clock pulses so as to provide a measure of a rate of wear of the magnetic head; and
   means for detecting a position of rotation of said rotating magnetic head device and supplying a detected output thereof to said measuring means;
   wherein said measuring means measures the rate of wear of the magnetic head at the detected position of rotation obtained from the detecting means, based on a variation in the oscillating frequency of said magnetic sensor and;
   wherein when a frequency of the reference clock pulses utilized by said measuring means is increased an interval in which the wear rate is measured is decreased and the accuracy of the wear rate measurement is improved.

2. The noncontact type magnetic head wear-rate measuring apparatus according to claim 1, wherein said measuring means includes,
   a variable oscillator circuit for deriving a variation in inductance due to a change in magnetic resistance of a detecting coil of said magnetic sensor and outputting an oscillating frequency according to said variation,
   a digital measuring circuit for outputting measured data proportional to the output of said variable oscillator circuit,
   wherein said outputted measured data supplied to said measuring means are stored in a storage unit to be compared to a predetermined wear rate value and said storage unit stores the initial value of the rate of head wear, and
   a rate-of-wear calculation unit for calculating the rate of wear of the magnetic head in response to the output of said digital measuring circuit.

3. The noncontact type magnetic head wear-rate measuring apparatus according to claim 2, wherein said magnetic head device has a rotational drum and further comprising means for detecting a rotational reference position of a rotational drum, and
   wherein a detected pulse obtained from said rotational position detecting means is supplied to said digital measuring circuit where frequency-divided pulses for dividing one turn of the drum into n (where n represents a number of regions of the drum) are determined,
   whereby said addresses positioned to mount the magnetic head to the drum as viewed from said rotational reference position are determined, and measurement start addresses are specified while said addresses are shifted in sequence.

4. The noncontact type magnetic head wear-rate measuring apparatus according to claim 2,
   wherein said digital measuring circuit includes first and second counters,
   said first counter is supplied with a train of pulses of a measured oscillating frequency to generate a pulse having a pulse width up to the counting of a predetermined number of pulses,
   said second counter is supplied with the generated pulse to count the number of the reference clock pulses lying within the pulse width, and
   the resultant counter output data corresponds to a clearance between said magnetic sensor and said magnetic head.

5. The noncontact type magnetic head wear-rate measuring apparatus according to claim 1,
   wherein the counter output data corresponding to the clearance between said magnetic sensor and said magnetic head is used as initial value data for determining the rate of head wear, at a stage prior to the use of said magnetic head.

6. The noncontact type magnetic wear-rate measuring apparatus according to claim 5,
   wherein the difference between the counter output data obtained from the result of measurement when said magnetic head is in use and said initial value data is compared with a reference value to determine the rate of wear of said magnetic head.

7. The noncontact type magnetic head wear-rate measuring apparatus according to claim 3, wherein a rotational position address at which said magnetic head is completely opposed to said magnetic sensor, is determined at the stage prior to the use of said magnetic head, based on a plurality of pieces of measured information obtained by sequentially shifting measurement start timing, and the rotational position address is thereafter specified so that the rate wear of said magnetic head is calculated.

8. The noncontact type magnetic head wear-rate measuring apparatus according to claim 1, wherein said magnetic sensor is fixed to and placed in said position.

9. The noncontact type magnetic head wear-rate measuring apparatus according to claim 1, wherein said magnetic sensor comprises an inverted U-shaped frame core and a detecting coil wound in a winding groove defined in the core.

10. The noncontact type magnetic head wear-rate measuring apparatus according to claim 9, wherein the width of said winding groove is wider than the width of a gap of said magnetic head and narrower than the width of said magnetic head.

11. The noncontact type magnetic head wear-rate measuring apparatus according to claim 1, wherein said rotating magnetic head device has a plurality of magnetic heads disposed so as to have predetermined steplike offsets relative to each other in the direction of rotation of said rotating magnetic head device, and said magnetic sensor has a height corresponding to a value larger than the sum of heights of said plurality of magnetic heads.

* * * * *